(12) United States Patent
Dahl

(10) Patent No.: US 7,079,892 B2
(45) Date of Patent: Jul. 18, 2006

(54) SYSTEM AND METHOD OF CARDIAC STIMULATION AT OBLIQUE VEIN

(75) Inventor: Roger Dahl, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 491 days.

(21) Appl. No.: 10/082,967

(22) Filed: Feb. 25, 2002

(65) Prior Publication Data

US 2003/0163164 A1 Aug. 28, 2003

(51) Int. Cl.
*A61N 1/39* (2006.01)
*A61N 1/372* (2006.01)

(52) U.S. Cl. .......................................... 607/5; 607/122
(58) Field of Classification Search ................ 607/4–5
See application file for complete search history.

(56) References Cited

U.S. PATENT DOCUMENTS

| | | | | |
|---|---|---|---|---|
| 5,107,834 A | * | 4/1992 | Ideker et al. | 607/5 |
| 5,224,476 A | * | 7/1993 | Ideker et al. | 607/9 |
| 5,376,103 A | | 12/1994 | Anderson et al. | |
| 5,690,686 A | * | 11/1997 | Min et al. | 607/5 |
| 5,978,705 A | * | 11/1999 | KenKnight et al. | 607/5 |
| 6,449,506 B1 | * | 9/2002 | Sh. Revishvili et al. | 607/5 |
| 6,456,876 B1 | * | 9/2002 | Kroll | 607/4 |
| 6,556,873 B1 | * | 4/2003 | Smits | 607/122 |
| 6,658,289 B1 | * | 12/2003 | Helland | 607/4 |
| 2002/0065544 A1 | | 5/2002 | Smits | |
| 2002/0103506 A1 | * | 8/2002 | Helland | 607/4 |

FOREIGN PATENT DOCUMENTS

| | | |
|---|---|---|
| DE | 100 58 105 A1 | 11/2000 |
| EP | 1 127 587 A2 | 8/2001 |

* cited by examiner

*Primary Examiner*—Robert E. Pezzuto
*Assistant Examiner*—Kristen Mullen
(74) *Attorney, Agent, or Firm*—Daniel G. Chapik; Girma Wolde-Michael; Paul H. McDowall

(57) ABSTRACT

A method includes placing a first electrode into electrical contact with a first portion of the heart, placing a second electrode into electrical contact with a second portion of the heart, and transmitting an electrical pulse between the first electrode and the second electrode in response to a determination that a cardiac event is detected.

17 Claims, 6 Drawing Sheets

SYSTEM AND METHOD OF CARDIAC STIMULATION AT OBLIQUE VEIN

BACKGROUND OF THE INVENTION

The present invention generally relates to implantable medical device systems and, more specifically, to an apparatus and method for defibrillating one or more portions of a heart.

DESCRIPTION OF THE RELATED ART

Various methods have been developed over the years to treat coronary arrhythmia, for example atrial and ventricular fibrillation. Broadly, atrial fibrillation represents the loss of synchrony between the atria and the ventricles. Atrial fibrillation, in general, may be characterized as a storm of electrical energy that travels in spinning wavelets across both atria, causing these upper chambers of the heart to quiver or fibrillate at rates of up to 600 times per minute. A broad range of physical symptoms may be associated with atrial fibrillation, including shortness of breath, profuse sweating, chest pain, dizziness, passing out, exercise intolerance, extreme fatigue, and the like.

In addition to the use of medications, ablation, pacing and invasive surgery, atrial fibrillation may be treated through the use of an implanted atrial defibrillator. The device electrically converts the arrhythmia by delivering an electrical shock to the atria via one or more leads placed in the heart. Typically, such a lead is fed through the venous system and attached to the wall of the atrium. However, it is generally desirable to apply the electrical shock only to the atria; otherwise, the ventricles may be inadvertently caused to fibrillate.

Similarly, ventricular fibrillation is a very rapid, uncoordinated, ineffective series of contractions in the ventricles of the heart. In this condition, the ventricles cannot effectively pump blood from the heart. Ventricular fibrillation, unless stopped, is typically fatal. If it is believed that a patient is likely to experience ventricular fibrillation, a ventricular defibrillator may be implanted in the patient. Such devices also include one or more leads that are fed through the venous system and are attached to the wall of one or both ventricles. An electrical shock is delivered directly to the ventricles to convert the arrhythmia to a normal rhythm. It is generally more efficacious, however, to apply the electrical shock such that the shocking current passes through both ventricles.

The present invention is directed to overcoming, or at least reducing, the effects of one or more of the problems set forth above.

SUMMARY OF THE INVENTION

In one aspect of the present invention, a method for defibrillating a heart is provided. The method includes placing a first electrode into electrical contact with a first portion of the heart, placing a second electrode into electrical contact with a second portion of the heart, and transmitting an electrical pulse between the first electrode and the second electrode in response to a determination that a cardiac event is detected.

In another aspect of the present invention, a medical device is provided. The medical device includes a control unit capable of outputting a defibrillating pulse and a first lead having a proximal end portion coupled with the control unit and a first electrode electrically coupled with the control unit and disposed distally from the proximal end portion of the first lead, wherein the first lead is capable of being routed through a venous system of a body such that the first electrode is electrically coupled with a wall of a right atrium of a heart. Further, the medical device includes a second lead having a proximal end portion coupled with the control unit and a second electrode electrically coupled with the control unit and disposed distally from the proximal end portion of the second lead, wherein the second lead is capable of being routed through the venous system of the body such that the second electrode is electrically coupled with a wall of an oblique vein.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which.

Figure 1:
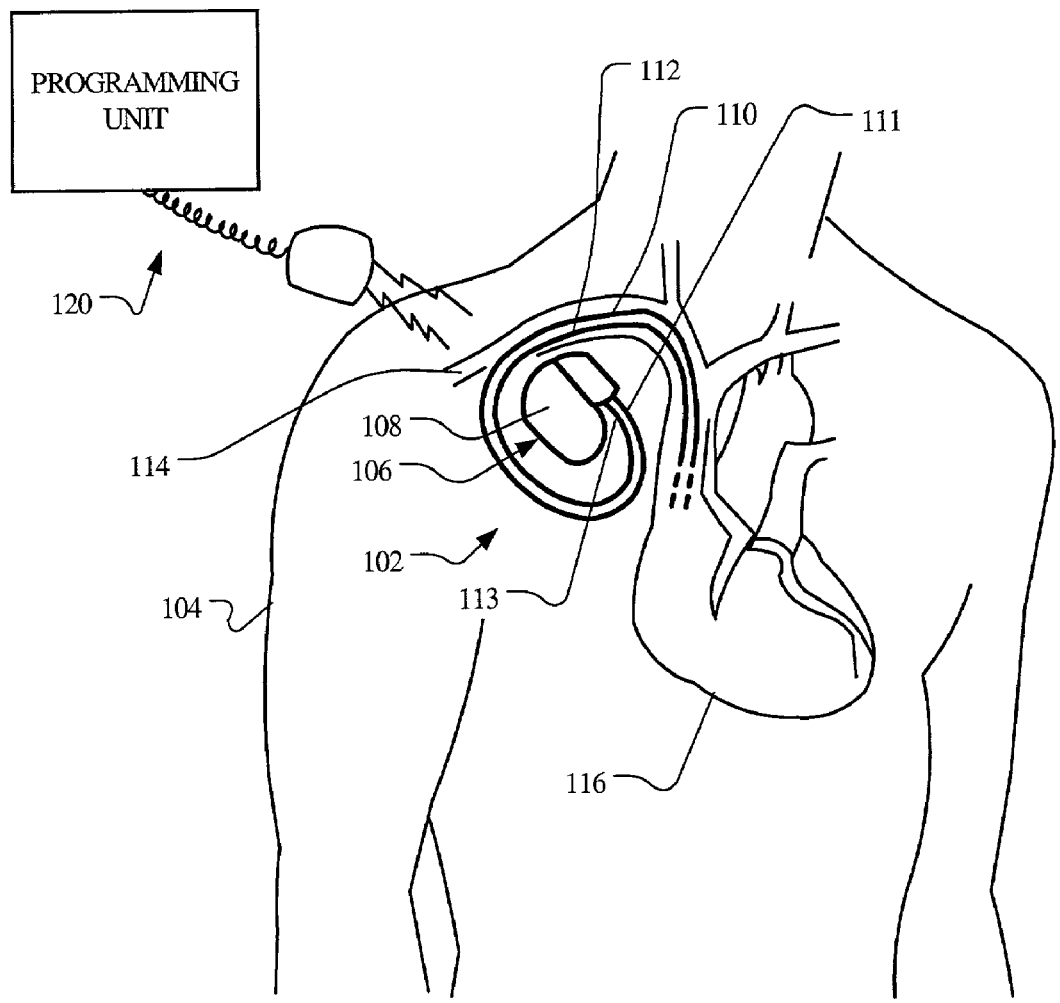
FIG. 1 is a stylized view of a coronary defibrillating device according to the present invention, which has been implanted in a human body.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and businessrelated constraints, which will vary from one implementation to another. Moreover, it will be appreciated that such a development effort might be complex and time-consuming but would nevertheless be a routine undertaking for those of ordinary skill in the art having the benefit of this disclosure.

The present invention encompasses a device and method for defibrillating atria and/or ventricles of a heart. FIG. 1 illustrates a first embodiment of an implantable defibrillator 102 according to the present invention that is implanted in a patient 104. The implantable defibrillator 102 includes an implantable electronic device 106 (e.g., a control unit or the like) housed within a hermetically-sealed, biologically-inert canister 108. A first lead 110 and a second lead 112 have proximal end portions 111, 113, respectively, that are electrically coupled to the implantable electronic device 106. The first lead 110 and the second lead 112 each extend via a vein 114 of the patient 104 to or proximate a heart 116, as will be described later. The implantable medical device 102 may be programmed by using a programming unit 120, which may send instructions to and receive information from the implantable defibrillator 102 via wireless (e.g., radio-frequency or the like) signals.

Figure 2:
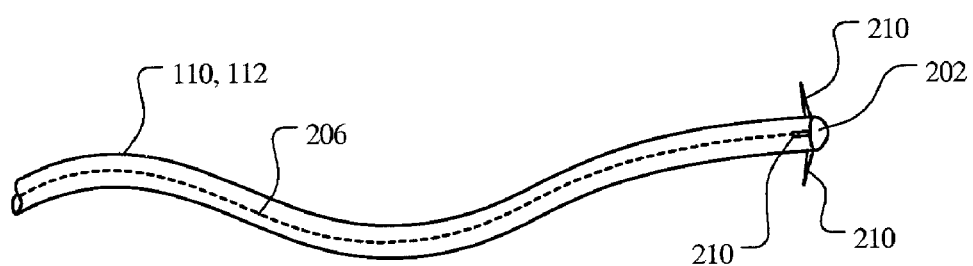
FIG. 2 is a stylized perspective view of a first embodiment of a lead for the coronary defibrillating device of FIG. 1.

In a first embodiment of a defibrillation device and leads according to the present invention, as shown in FIG. 2, each of the first lead 110 and the second lead 112 includes an exposed, electrically-conductive tip electrode 202 disposed distally from the proximal end portions 111, 113 (shown in FIG. 1) of the leads 110, 112. When in place, the tip electrode 202 is electrically coupled with body tissue and is used to deliver an electrical shock to a portion of the heart 116 or to receive an electrical signal from a portion of the heart 116. The lead 110, 112 also includes a conductor set 206 electrically coupling the implantable electronic device 106, or an electrical extension (not shown) extending from the implantable electronic device 106, and the tip electrode 202. The leads 110, 112 may also include one or more anchoring members 210 for anchoring the lead 110, 112 to tissue, as will be described later.

Figure 3:
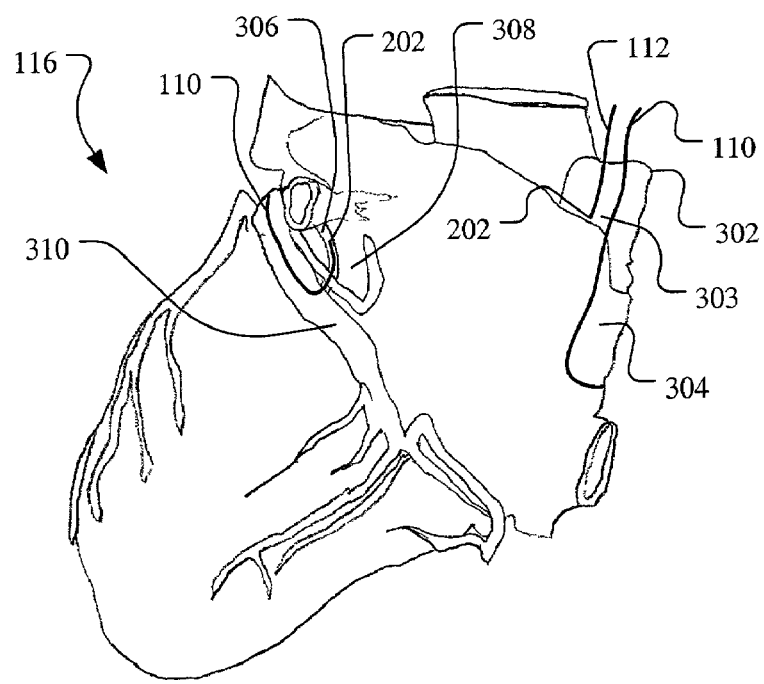
FIG. 3 is a partial stylized view of a first embodiment of the coronary defibrillation device of FIG. 1.

FIG. 3 illustrates a posterior view of the heart 116 including a superior vena cava 302 extending to a right atrium 304 and an oblique vein 306 extending over a left atrium 308 to a coronary sinus 310. According to the present invention, the first lead 110 is fed through the body's venous system (e.g., through a subclavian vein (not shown) or the like), through the superior vena cava 302, and into the right atrium 304. The first lead 110 is then fed into and through the coronary sinus 310 and into the oblique vein 306 such that the tip electrode 202 of the first lead 110 is electrically coupled with a portion of the oblique vein 306. In one embodiment, the first lead 110 is attached to a portion of the oblique vein 306 by one or more of the anchoring members 210. The second lead 112 is fed through the body's venous system (e.g., through the subclavian vein or the like) through the superior vena cava 302 and to a lower portion 303 of the superior vena cava 303 such that the tip electrode 202 of the second lead 112 is electrically coupled with the lower portion 303 of the superior vena cava 302. In one embodiment, the second lead 112 is attached to a wall of the lower portion 303 of the superior vena cava 302 by one or more of the anchoring members 210.

Upon determining that the heart 116 is experiencing atrial fibrillation, an electric defibrillation pulse or pulses are transmitted between the tip electrode 202 of the first lead 110 and the tip electrode 202 of the second lead 112 through the right atrium 304 and the left atrium 308. The defibrillation pulse or pulses may be useful in reducing the undesirable fibrillation so that the atria may regain a more normal rhythm either by natural means or through pacing signals. The defibrillation pulse or pulses may be in the form of a uniphasic pulse, in which electrical energy travels in one direction substantially between the tip electrode 202 of the first lead 110 and the tip electrode 202 of the second lead 112 through the right atrium 304 and the left atrium 308.

Alternatively, the electric energy may be in the form of biphasic pulses, in which the electrical energy first travels in one direction between the tip electrode 202 of the first lead 110 and the tip electrode 202 of the second lead 112 through the right atrium 304 and the left atrium 308, then travels in the opposite direction between the tip electrode 202 of the first lead 110 and the tip electrode 202 of the second lead 112 through the right atrium 304 and the left atrium 308. For example, the biphasic pulses may comprise a first pulse traveling from the tip electrode 202 of the first lead 110 to the tip electrode 202 of the second lead 112 through the right atrium 304 and the left atrium 308, and a second pulse traveling from the tip electrode 202 of the second lead 112 to the tip electrode 202 of the first lead 110 through the right atrium 304 and the left atrium 308.

Figure 4:
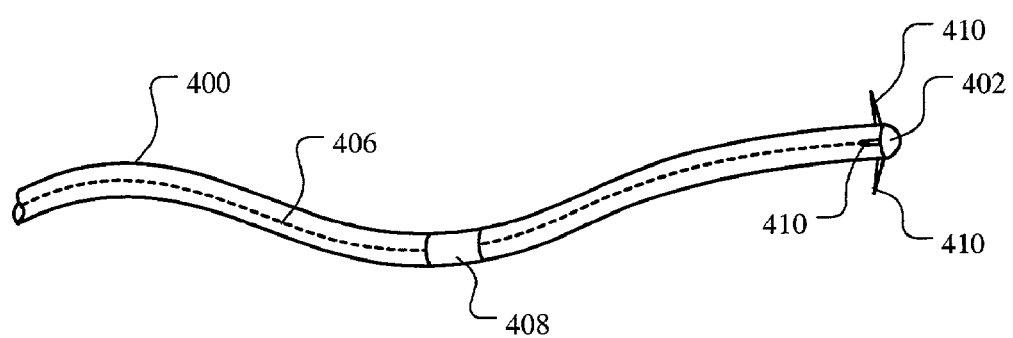
FIG. 4 is a stylized perspective view of a second embodiment of a lead for the coronary defibrillating device of FIG. 1.
Figure 5:
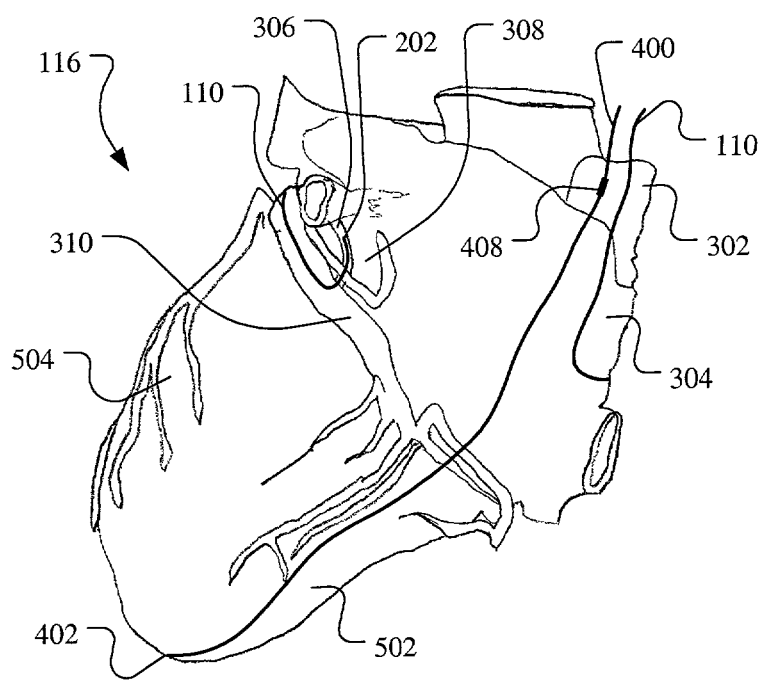
FIG. 5 is a partial stylized view of a second embodiment of the coronary defibrillation device of FIG. 1.

FIGS. 4 and 5 respectively illustrate a second embodiment of a lead and a defibrillation device and its implementation, according to the present invention. As in the lead 112, a lead 400 includes an exposed, electrically-conductive tip electrode 402 disposed distally from a proximal end portion (not shown) of the lead 400. However, in this embodiment, the tip electrode 402 is used to deliver electrical energy to and/or receive electrical energy from a wall of a right ventricle 502. The lead 400 includes a conductor set 406 electrically coupling the implantable electronic device 106, or an electrical extension (not shown) extending from the implantable electronic device 106, and the tip electrode 402. The conductor set 406 also electrically couples a ring electrode 408, disposed intermediate the proximal end portion of the lead and the tip electrode 402, and the implantable electronic device 106, either directly or via the electrical extension. While the present invention is described relative to the ring electrode 408, the electrode may have any desired shape and size. The lead 400 may also include one or more anchoring members 410 for anchoring the lead to the wall of the right ventricle 502.

As illustrated in FIG. 5, the first lead 110 is routed as described in the first embodiment (shown in FIG. 3). The lead 400 is routed through the superior vena cava 302, through the right atrium 304, and into the right ventricle 502, such that the tip electrode 402 is electrically coupled with the wall of the right ventricle 502 and the ring electrode 408 is electrically coupled with the lower portion 303 of the superior vena cava 302. In this embodiment, a defibrillation pulse or pulses, originating from the device 106, may be transmitted between the ring electrode 408 and the tip electrode 202 of the first lead 110, through the right atrium 304 and the left atrium 308, to defibrillate the right atrium 304 and the left atrium 308. Further a defibrillation pulse or pulses may be transmitted between the tip electrode 402 of the lead 400 and one or both of the tip electrode 202 of the first lead 110 and the ring electrode 408, through the right ventricle 502 and/or a left ventricle 504, to defibrillate the right ventricle 502 and/or the left ventricle 504.

As in the first embodiment (shown in FIGS. 2 and 3), the electrical energy transmitted between the tip electrode 402 of the lead 400 and one or both of the tip electrode 202 of the first lead 110 and the ring electrode 408 may be uniphasic in either direction (i.e., from the tip electrode 402 of the lead 400 to one or both of the tip electrode 202 of the first lead 110 and the ring electrode 408 or from one or both of the tip electrode 202 of the first lead 110 and the ring electrode 408 to the tip electrode 402 of the lead 400). Further, the electrical energy transmitted between the tip electrode 402 of the lead 400 and one or both of the tip electrode 202 of the first lead 110 and the ring electrode 408 may be biphasic (i.e., first traveling in one direction between the tip electrode 402 of the lead 400 and one or both of the tip electrode 202 of the first lead 110 and the ring electrode 408 and then in the opposite direction).

Figure 6:
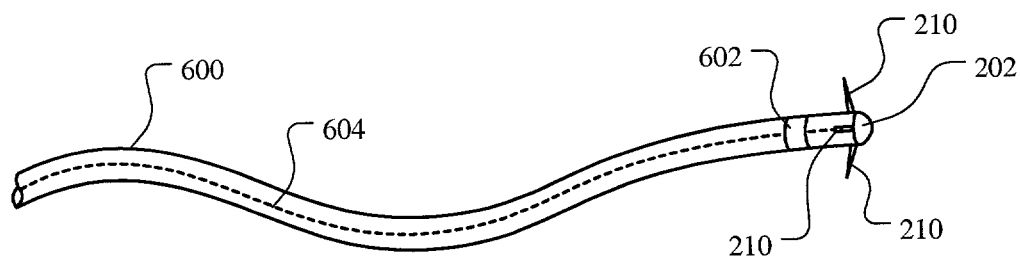
FIG. 6 is a stylized perspective view of a third embodiment of a lead for the coronary defibrillating device of FIG. 1.

The implantable defibrillator 102, including various embodiments of leads 110, 112, 400, may include a capability of sensing heart rhythm or the like in one or more locations of the heart 116. For example, in a third embodiment of a lead according to the present invention illustrated in FIG. 6, a lead 600 includes a sensing electrode 602 electrically coupled with the implantable electronic device 106 via the conductor set 604. Other aspects of the lead 600 may be, but are not required to be, common with the lead 110, 112 (shown in FIG. 2) and are illustrated in FIG. 6 (e.g., the tip electrode 202, the anchoring members 210, and the like).

Figure 7:
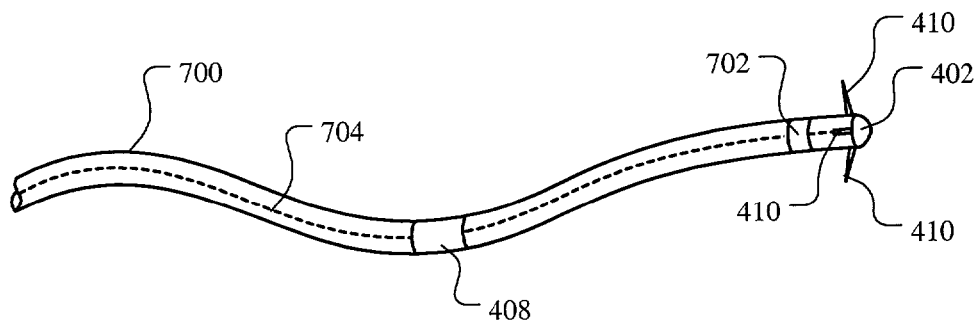
FIG. 7 is a stylized perspective view of a fourth embodiment of a lead for the coronary defibrillating device of FIG. 1.

Further, in a fourth embodiment of a lead according to the present invention, as illustrated in FIG. 7, a lead 700 includes a sensing electrode 702 electrically coupled with the implantable electronic device 106. Other aspects of the lead 700 may be, but are not required to be, common with the lead 400 (shown in FIG. 4) and are illustrated in FIG. 7 (e.g., the tip electrode 402, the ring electrode 408, the anchoring members 410, and the like). While a particular configuration and location of the sensing electrodes 602, 702 are shown in FIGS. 6 and 7, respectively, any desired configuration and location is encompassed by the present invention.

Figure 8:
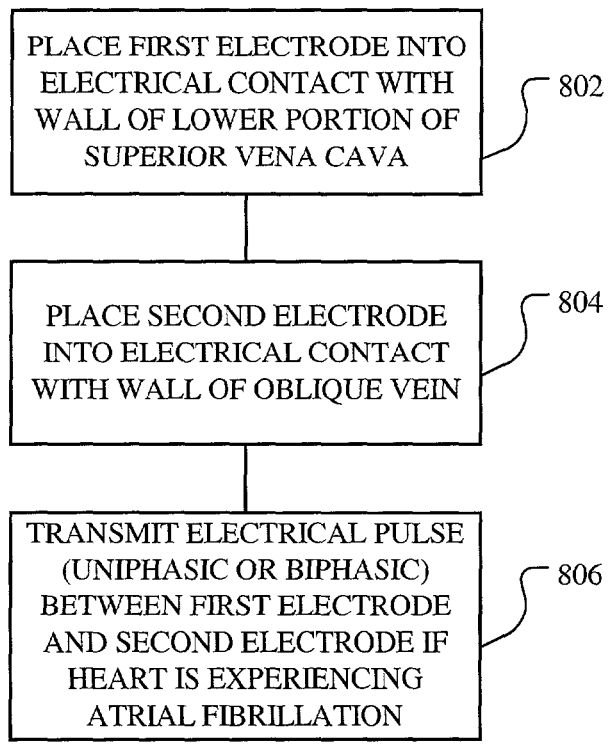
FIG. 8 is a flow chart of a first embodiment of a method according to the present invention.

A first embodiment of a method for defibrillating a heart is illustrated in FIG. 8. The method includes placing a first electrode into electrical contact with a wall of a lower portion of a superior vena cava (block 802) and placing a second electrode into electrical contact with a wall of an oblique vein (block 804). The method further comprises transmitting an electrical pulse between the first electrode and the second electrode if the heart is experiencing atrial fibrillation (block 806). The electrical pulse delivered to the heart may be a uniphasic pulse or a biphasic pulse. The pulse delivered to the heart may be delivered using one of the leads described in FIGS. 2, 4, 6, and 7.

Figure 9:
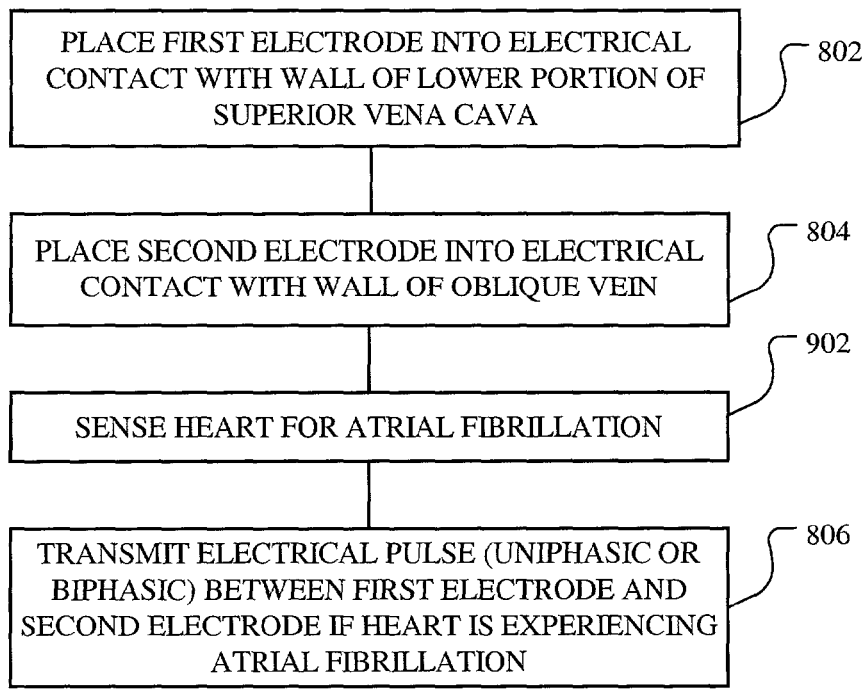
FIG. 9 is a flow chart of a second embodiment of a method according to the present invention.

In a second embodiment illustrated in FIG. 9, the method of FIG. 8 further comprises sensing the heart for atrial fibrillation (block 902). In one embodiment, the device 106 may determine that the heart is experiencing atrial fibrillation based upon one or more electrical signals received from the heart and may provide a pulse in response to the determination.

Figure 10:
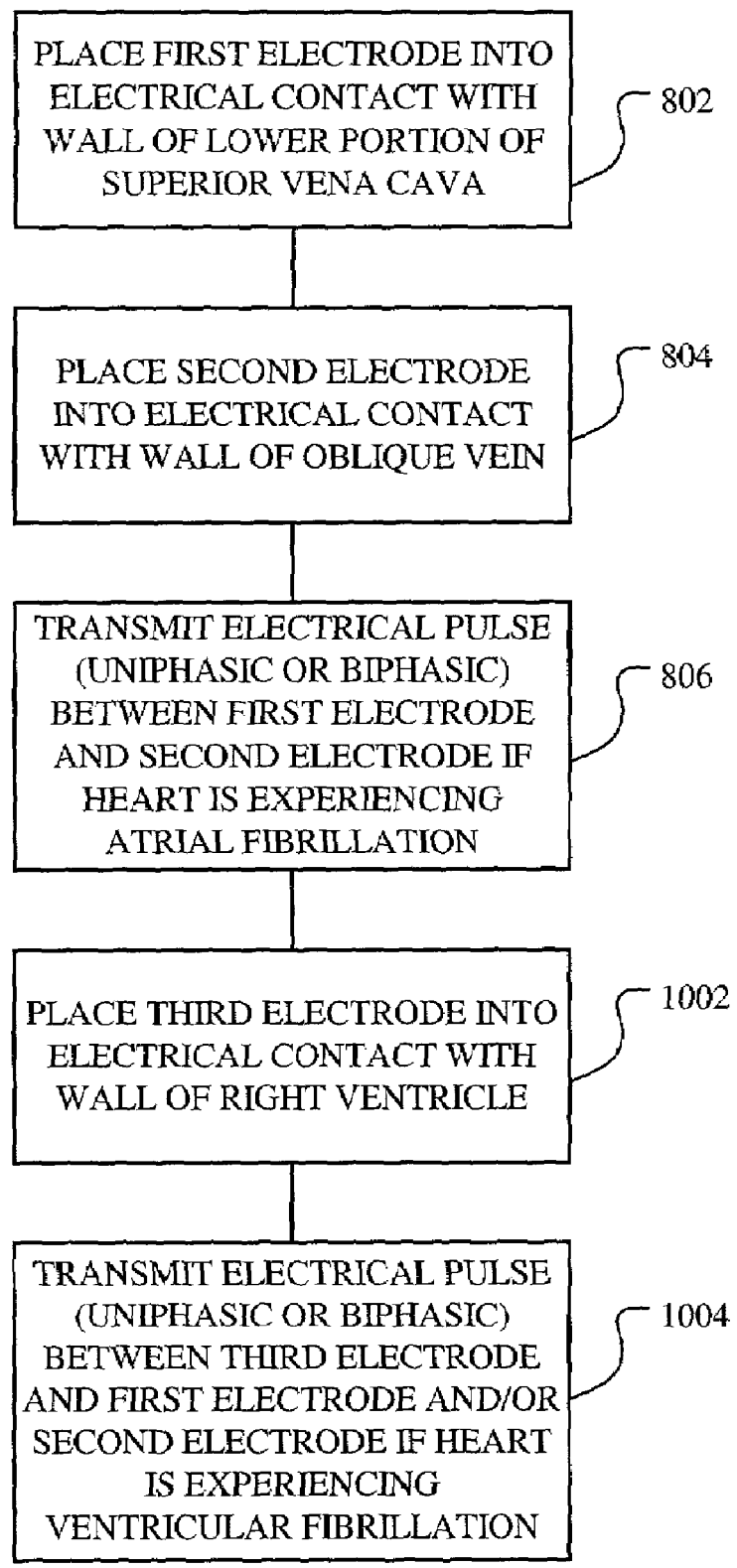
FIG. 10 is a flow chart of a third embodiment of a method according to the present invention.

In a third embodiment of a method for defibrillating a heart, as illustrated in FIG. 10, the method of FIG. 8 further includes placing a third electrode into electrical contact with a wall of a right ventricle of the heart (block 1002) and transmitting an electrical pulse between the third electrode and at least one of the first and second electrodes if the heart is experiencing ventricular fibrillation (block 1004). The electrical pulse may be a uniphasic pulse or a biphasic pulse.

Figure 11:
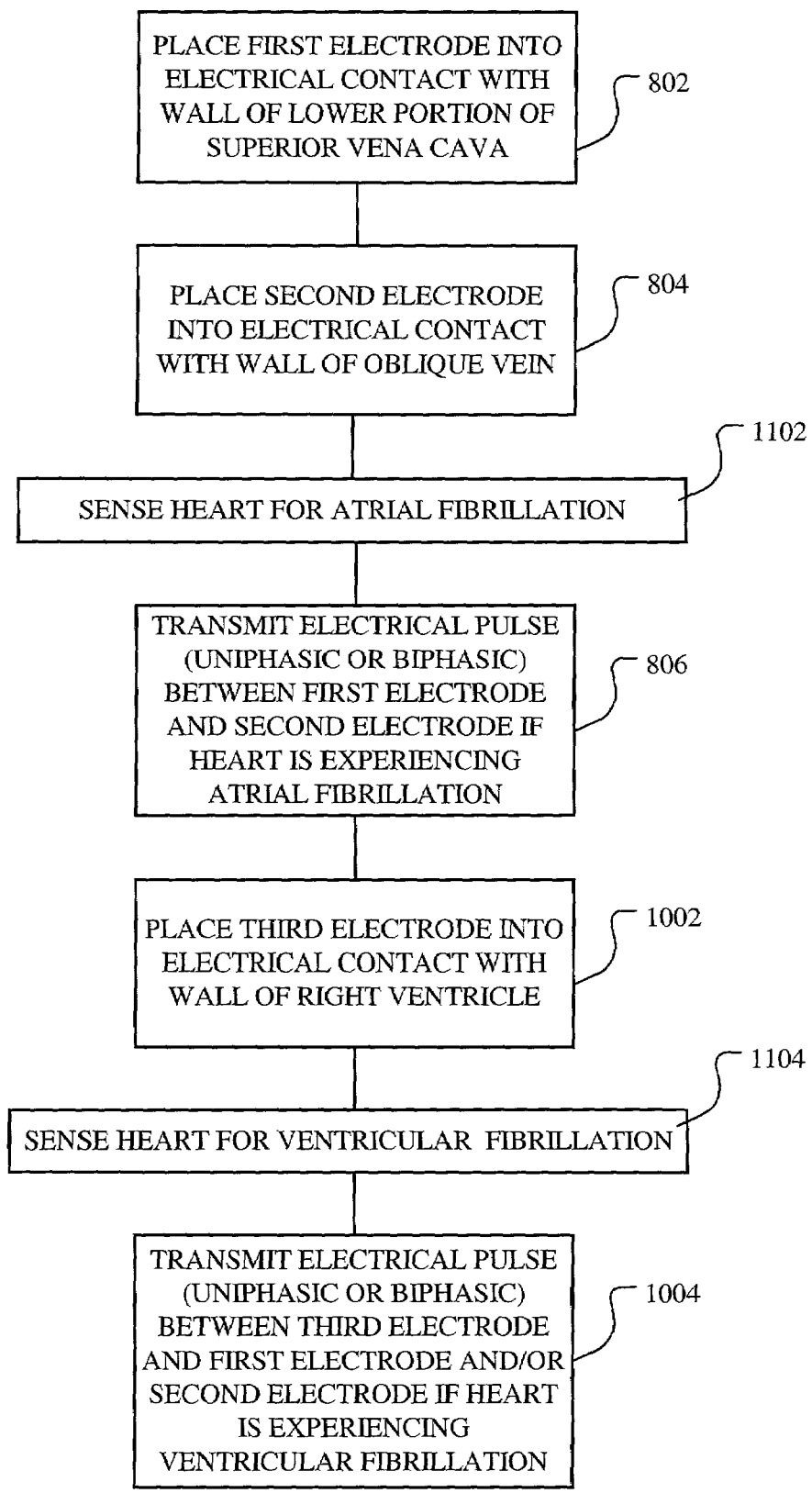
FIG. 11 is a flow chart of a fourth embodiment of a method according to the present invention.

In a fourth embodiment illustrated in FIG. 11, the method of FIG. 10 further includes sensing the heart for atrial fibrillation (block 1102) and/or ventricular fibrillation (block 1104).

Thus, the present invention provides a way for a defibrillation pulse or pulses to be delivered specifically to the atria, if atrial fibrillation is encountered and/or allows a defibrillation pulse to be delivered through both ventricles if the ventricles are in fibrillation. Using embodiments of the present invention, more than one portion of the heart (e.g., the right atrium 304, the left atrium 308, the right ventricle 502, the left ventricle 504, or the like) may be stimulated substantially simultaneously in response to a cardiac event detected by the implantable electronic device 106.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for defibrillating a heart, comprising:
    placing a first electrode into physical contact with a first portion of the heart, wherein the first portion of the heart is proximate a superior vena cava;
    placing a second electrode into physical contact with a second portion of the heart, wherein the second portion of the heart is an interior wall of an oblique vein; and
    transmitting an electrical pulse between the first electrode and the second electrode in response to a determination that a cardiac event is detected.

2. The method of claim 1, wherein the electrical pulse is a defibrillating waveform traveling between a location proximate the superior vena cava and the oblique vein.

3. A method, according to claim 1, wherein transmitting the electrical pulse further comprises transmitting the electrical pulse between the first electrode and the second electrode in response to a determination of atrial fibrillation.

4. A method, according to claim 1, wherein transmitting the electrical pulse further comprises transmitting a uniphasic electrical pulse between the first electrode and the second electrode.

5. A method, according to claim 1, wherein transmitting the electrical pulse further comprises transmitting a biphasic electrical pulse between the first electrode and the second electrode.

6. A method, according to claim 1, further comprising:
    placing a third electrode into contact with a wall of a right ventricle of the heart; and
    transmitting an electrical pulse between the third electrode and at least one of the first and second electrodes if the heart is experiencing ventricular fibrillation.

7. A method, according to claim 6, further comprising sensing the heart for ventricular fibrillation.

8. A method, according to claim 6, wherein transmitting the electrical pulse further comprises transmitting a uniphasic electrical pulse between the third electrode and at least one of the first and second electrodes.

9. A method, according to claim 6, wherein transmitting the electrical pulse further comprises transmitting a biphasic electrical pulse between the third electrode and at least one of the first and second electrodes.

10. An apparatus for defibrillating a heart, comprising:
    means for placing a first electrode into physical contact with a first portion of the heart proximate a superior vena cava of the heart;

means for placing a second electrode into physical contact with a second portion of the heart within an oblique vein of the heart accessible via a coronary sinus of the heart; and means for transmitting an electrical pulse between the first electrode and the second electrode in response to a determination that a cardiac event is detected.

11. An apparatus, according to claim 10, wherein means for transmitting the electrical pulse further comprises means for transmitting the electrical pulse between the first electrode and the second electrode in response to a determination that atrial fibrillation is detected.

12. An apparatus, according to claim 10, wherein the means for transmitting the electrical pulse further comprises means for transmitting a uniphasic electrical pulse between the first electrode and the second electrode.

13. An apparatus, according to claim 10, wherein the means for transmitting the electrical pulse further comprises means for transmitting a biphasic electrical pulse between the first electrode and the second electrode.

14. An apparatus, according to claim 10, further comprising:

means for placing a third electrode into contact with a wall of a right ventricle of the heart; and means for transmitting an electrical pulse between the third electrode and at least one of the first and second electrodes if the heart is experiencing ventricular fibrillation.

15. An apparatus, according to claim 14, further comprising means for sensing the heart for ventricular fibrillation.

16. An apparatus, according to claim 14, wherein the means for transmitting the electrical pulse further comprises means for transmitting a uniphasic electrical pulse between the third electrode and at least one of the first and second electrodes.

17. An apparatus, according to claim 14, wherein the means for transmitting the electrical pulse further comprises means for transmitting a biphasic electrical pulse between the third electrode and at least one of the first and second electrodes.

* * * * *